United States Patent
Spahn

(10) Patent No.: US 7,426,261 B2
(45) Date of Patent: Sep. 16, 2008

(54) X-RAY SYSTEM, AND METHOD USING AN X-RAY SYSTEM

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 113 days.

(21) Appl. No.: 11/349,136

(22) Filed: Feb. 8, 2006

(65) Prior Publication Data

US 2006/0188071 A1    Aug. 24, 2006

(30) Foreign Application Priority Data

Feb. 9, 2005  (DE) .................. 10 2005 005 902

(51) Int. Cl.
*H05G 1/64* (2006.01)
*H01L 27/146* (2006.01)

(52) U.S. Cl. .................. 378/98.8; 378/98; 378/98.2; 378/116; 250/363.08; 250/370.09

(58) Field of Classification Search ............ 378/4–20, 378/98, 98.2, 98.6, 116, 98.8; 250/363.01, 250/363.08, 370.01, 370.04, 370.08, 370.09
See application file for complete search history.

(56) References Cited

U.S. PATENT DOCUMENTS

| | | | | |
|---|---|---|---|---|
| 3,763,375 A | * | 10/1973 | Scheninger | .......... 378/177 |
| 4,893,323 A | * | 1/1990 | Cook, III | .......... 378/208 |
| 5,311,883 A | * | 5/1994 | Sherman | .......... 128/846 |
| 5,514,873 A | * | 5/1996 | Schulze-Ganzlin et al. | . 250/394 |
| 5,877,501 A | * | 3/1999 | Ivan et al. | .......... 250/370.09 |
| 5,920,606 A | * | 7/1999 | Sohr | .......... 378/177 |
| 7,189,972 B2 | * | 3/2007 | Ertel et al. | .......... 250/370.11 |
| 2002/0150214 A1 | * | 10/2002 | Spahn | .......... 378/189 |
| 2003/0194056 A1 | * | 10/2003 | Spahn | .......... 378/205 |
| 2004/0188625 A1 | * | 9/2004 | Schulze-Ganzlin | .... 250/370.09 |
| 2005/0207534 A1 | * | 9/2005 | Petrick et al. | .......... 378/114 |
| 2007/0012879 A1 | * | 1/2007 | Testardi | .......... 250/361 R |
| 2007/0048566 A1 | * | 3/2007 | Nakamura et al. | .......... 429/22 |
| 2007/0116180 A1 | * | 5/2007 | Omernick et al. | .......... 378/116 |
| 2007/0140424 A1 | * | 6/2007 | Serceki | .......... 378/62 |
| 2007/0165783 A1 | * | 7/2007 | Abu Tabanjeh | .......... 378/116 |

FOREIGN PATENT DOCUMENTS

DE   101 18 745 C2   3/2003

* cited by examiner

*Primary Examiner*—Edward J. Glick
*Assistant Examiner*—Anastasia Midkiff
(74) *Attorney, Agent, or Firm*—Harness, Dickey & Pierce, P.L.C.

(57) ABSTRACT

An X-ray system includes a radiation source, a central control device, a mobile solid object detector, and a wireless communication link between the solid object detector and the control device. For an examination to run correctly, the mobile solid object detector includes a signaling unit for indicating an existing association with the central control unit.

20 Claims, 1 Drawing Sheet

X-RAY SYSTEM, AND METHOD USING AN X-RAY SYSTEM

The present application hereby claims priority under 35 U.S.C. §119 on German patent application number DE 10 2005 005 902.3 filed Feb. 9, 2005, the entire contents of which is hereby incorporated herein by reference.

FIELD

The invention generally relates to an X-ray system and/or to a method using an X-ray system.

BACKGROUND

An X-ray system or a method is known from DE 101 18 745 C2.

A digital X-ray system, in which a digital, mobile solid object detector and a central control device communicate wirelessly and bidirectionally with one another, has, inter alia, the advantage of being flexible and simple to handle even in the case of critical applications such as X-ray shots of patients who must not be moved. The mobility of the solid object detector indicates that a few problems may also arise in addition to many advantages, however: first, when there are a plurality of X-ray systems or a plurality of mobile solid object detectors there is the risk of confusion, so that, by way of example, the wrong solid object detector, that is to say the solid object detector which is not suitable for the examination or which is not part of the X-ray system, is put into a shooting position close to a patient. If X-ray radiation is then applied and an X-ray shot is triggered, the X-ray shot is remote from the patient and hence meaningless, while at the same time the X-ray radiation irradiating the wrong solid object detector close to the patient does not produce a good image, and secondly there is the risk that the wrong association indicates that a patient is exposed to unwanted irradiation.

SUMMARY

It is an object of at least one embodiment of the present invention to allow a digital X-ray examination using a wireless, mobile solid object detector to proceed correctly and in a simplified form.

At least one embodiment of the invention may achieve an object via an X-ray system or for a method.

In the inventive X-ray system of at least one embodiment, containing a radiation source, a central control device and an associatable wireless mobile solid object detector, the signaling unit can be used by a user to perform a simple and safe check on the distinct association between the mobile solid object detector and the central control device by virtue of an indicator confirming the association. This makes it possible to prevent the incorrect use of the solid object detector which is not part of the X-ray system or of X-ray radiation.

In accordance with one refinement of at least one embodiment of the invention, the signaling unit is provided in the form of a visual and/or audio indicator; the visual or audio indicator provides the user with a particularly good and distinct way of telling whether a solid object detector is the one associated with the X-ray system.

In accordance with a further refinement of at least one embodiment of the invention, the indicator covers the respective availability of the solid object detector. Thus, in addition to the association, it is a simple matter to tell whether the associated solid object detector is in an operating state in which it is not available for an X-ray shot. Availability can be indicated by way of a positive signal, for example, and a lack of availability can be indicated by way of a negative signal, for example.

BRIEF DESCRIPTION OF THE DRAWINGS

Embodiments of the invention and further advantageous refinements are explained in more detail in the description below, with reference to schematically shown example embodiments in the drawings, without this limiting the invention to these example embodiments. In the drawing.

DETAILED DESCRIPTION OF THE EXAMPLE EMBODIMENTS

Figure 1:
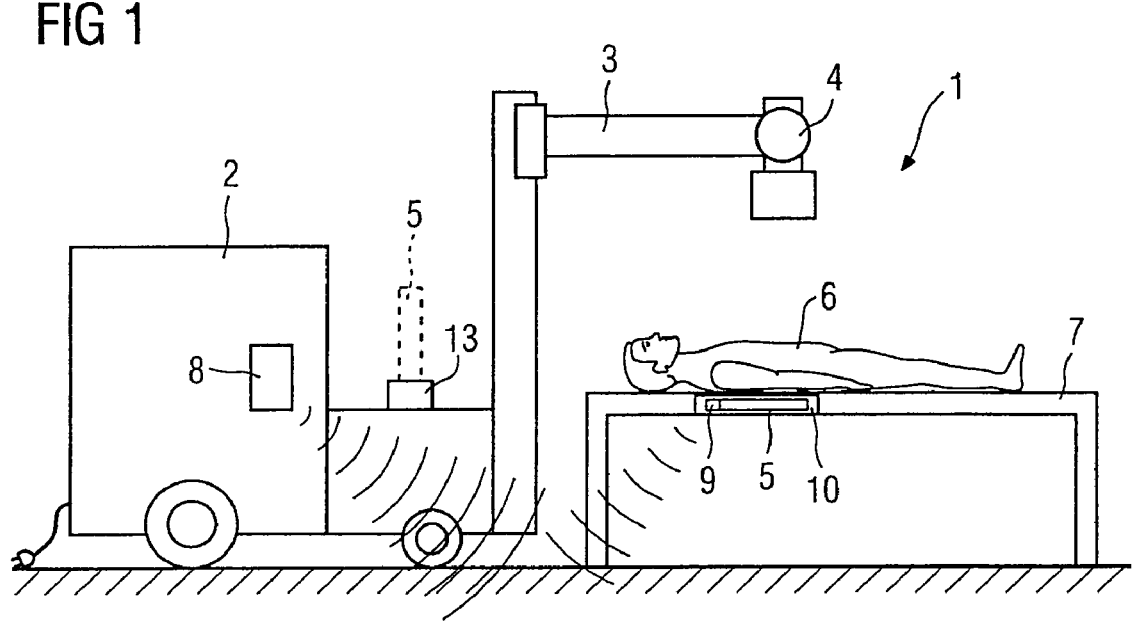
FIG. 1 shows a basic outline of an X-ray system based on a known system.

FIG. 1 shows an X-ray system 1 containing a central control device 2, a radiation source 4 arranged on a support arm 3, and an associated mobile solid object detector 5 which can be positioned remotely from the central control device. The solid object detector 5 can be used in a known manner to shoot X-ray images of a patient 6 lying on an operating table. The mobility of the solid object detector 5 indicates that it can be arranged as desired, for example including in a drawer 10 in the operating table 7, which is in the form of a Bucky table.

The control device 2 has a transmission and reception device 8, with a corresponding transmission and reception device 9 being provided on the radiation receiver. Both transmission and reception device 8, 9 can communicate with one another wirelessly and bidirectionally, for example in order to transmit control commands and image data. A charging station 13 on the central control device 2 can be used to recharge storage batteries provided in the solid object detector 5.

Figure 2:
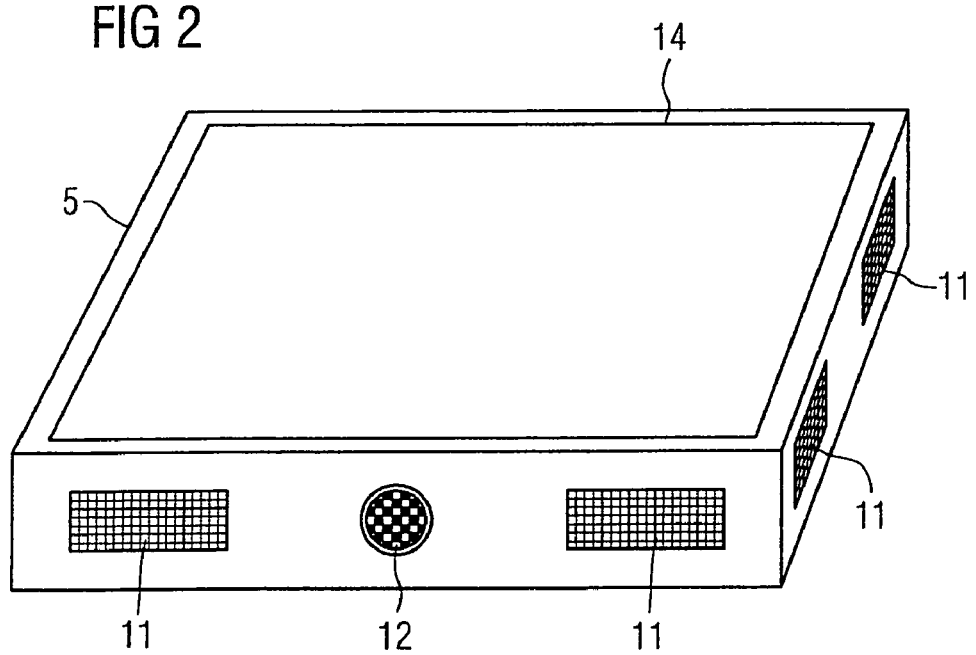
FIG. 2 shows a basic illustration of a solid object detector based on at least one embodiment of the invention.

FIG. 2 shows a solid object detector 5 based on at least one embodiment of the invention with a visual indicator fitted to its narrow sides in the form of LED arrays 11 and with an audio indicator, likewise fitted on one of its narrow sides, in the form of a loudspeaker 12. The indicators are arranged outside of the active image area 14 of the solid object detector 5, the active image area 14 being understood to be the region provided for converting X-ray radiation into depiction data. Components which are usual in solid object detectors, such as a pixel matrix, reading electronics and also transmission and reception devices and storage batteries, are not shown in more detail in order to allow for better clarity of the essence of at least one embodiment of the invention.

If an examination room now contains a plurality of solid object detectors or it is not absolutely clear that the solid object detector provided is actually the one associated with the X-ray system 1, the association needs to be checked before the X-ray shot. To this end, the central control device 2 sends an activation signal to the associated solid object detector 5 in order to check that it is present or that it is available. The associated solid object detector 5 then indicates an existing association by outputting a visual and/or audio signal.

By way of example, the LED arrays 11 may flash green in order to indicate the association and simultaneous availability, and may flash red in order to indicate the association and a lack of availability. Equally, various sounds which are output by the loudspeaker 12 may indicate the association.

Following confirmation, the associated solid object detector 5 can then be put into the shooting position for the patient and an X-ray shot can be taken. If the solid object detector in question does not output a signal then it is not the associated solid object detector 5; the search for the correct solid object detector can then be simplified by repeated triggering of the indicator.

If the solid object detector 5 is in the drawer 10 in the operating table 11 in the form of a Bucky table, a further refinement of at least one embodiment of the invention has provision for the Bucky table to be in a form such that the visual indicator on the associated mobile solid object detector 5 can be detected, when put into the drawer 10, via optical sensors arranged in the Bucky table and can be indicated by way of a visual signaling unit fitted on the outside of the Bucky table. The signaling unit may in turn comprise LEDs situated on the Bucky table. It is thus possible for the user to recognize a visual signal output by the solid object detector 5 even if the solid object detector 5 or at least its indicator is not outwardly visible.

At least one embodiment of the invention can be briefly summarized in the following manner: for an examination to run correctly, the mobile solid object detector 5 in an X-ray system 1, containing a radiation source 4, a central control device 2, a mobile solid object detector 5 which can be associated with the latter, and a wireless communication link between the solid object detector and the control device 2, has a signaling unit for indicating an existing association with the central control unit 2.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray system, comprising:
    a radiation source;
    a central control device;
    a mobile solid object detector to communicate with the control device via a wireless communication link, the mobile solid object detector including a signaling unit to indicate an existing association with the central control device, the signaling unit being provided in the form of a visual indicator on the mobile solid object detector; and
    a Bucky table; wherein
        the visual indicator on the mobile solid object detector is detectable, when put into a drawer in the Bucky table, via optical sensors arranged in the Bucky table and is indicatable by way of a visual signaling unit fitted on the outside of the Bucky table.

2. The X-ray system as claimed in claim 1, wherein the signaling unit further includes an audio indicator.

3. The X-ray system as claimed in claim 1, wherein the signaling unit also covers the respective availability of the solid object detector.

4. The X-ray system as claimed in claim 1, wherein the signaling unit is arranged on at least one narrow side of the solid object detector.

5. The X-ray system as claimed in claim 2, wherein the audio indicator includes at least one loudspeaker.

6. A method using an X-ray system including a radiation source, a central control device and a mobile solid object detector to communicate with the central control device via a wireless communication link, the method comprising:
    receiving, from the central control device, an activation signal at the mobile solid object detector; and
    indicating, at the mobile solid object detector via a signaling unit, an existing association between the mobile solid object detector and the central control device, the signaling unit being provided in the form of a visual indicator on the mobile solid object detector; wherein the visual indicator includes at least one LED,
        the visual indicator is detectable, when put into a drawer in a Bucky table, via optical sensors arranged in the Bucky table and is indicatable by way of a visual signaling unit fitted on the outside of the Bucky table.

7. The method as claimed in claim 6, wherein the indication by the signaling unit, further includes an audio indication.

8. The X-ray system as claimed in claim 1, wherein the signaling unit includes an audio indicator.

9. The X-ray system as claimed in claim 8, wherein the at least one indicator also covers the respective availability of the solid object detector.

10. The X-ray system as claimed in claim 3, wherein the indicator is arranged on at least one narrow side of the solid object detector.

11. The X-ray system as claimed in claim 8, wherein the at least one indicator is arranged on at least one narrow side of the solid object detector.

12. The X-ray system as claimed in claim 9, wherein the at least one indicator is arranged on at least one narrow side of the solid object detector.

13. An X-ray system, comprising:
    a radiation source;
    a central control device;
    a mobile solid object detector to communicate with the control device via a wireless communication link, the mobile solid object detector including a signaling unit to indicate an existing association with the central control device, the signaling unit being provided in the form of a visual indicator on the mobile solid object detector, the visual indicator including at least one LED; and
    a Bucky table; wherein
        the visual indicator on the mobile solid object detector is detectable, when put into a drawer in the Bucky table, via optical sensors arranged in the Bucky table and is indicatable by way of a visual signaling unit fitted on the outside of the Bucky table.

14. An X-ray system, comprising:
    a mobile solid object detector to communicate with a central controller via a wireless communication link;
    means for radiating x-rays;
    means for receiving, from the central controller, an activation signal at the mobile solid object detector;
    means for indicating, at the mobile solid object detector, an existing association between the mobile solid object detector and the central controller, the means for indicating being provided in the form of a visual indicator on the mobile solid object detector, the visual indicator including at least one LED; and
    a Bucky table; wherein
        the visual indicator is detectable, when put into a drawer in the Bucky table, via optical sensors arranged in the Bucky table and is indicatable by way of a visual signaling unit fitted on the outside of the Bucky table.

15. The X-ray system as claimed in claim 14, wherein the means for indicating further includes an audio indicator.

16. The X-ray system as claimed in claim 14, wherein the means for indicating also covers the respective availability of the solid object detector.

17. The X-ray system as claimed in claim 14, wherein the means for indicating is arranged on at least one narrow side of the solid object detector.

18. The X-ray system as claimed in claim 15, wherein the audio indicator includes at least one loudspeaker.

19. The X-ray system as claimed in claim 13, wherein the indicator also covers the respective availability of the solid object detector.

20. The X-ray system as claimed in claim 13, wherein the signaling unit is arranged on at least one narrow side of the solid object detector.

* * * * *